United States Patent
Cahan et al.

(10) Patent No.: US 11,076,246 B2
(45) Date of Patent: *Jul. 27, 2021

(54) EYE-MOUNTED HEARING AID

(71) Applicant: INTERNATIONAL BUSINESS MACHINES CORPORATION, Armonk, NY (US)

(72) Inventors: Amos Cahan, Netaim (IL); Katsuyuki Sakuma, Fishkill, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 102 days.

This patent is subject to a terminal disclaimer.

(21) Appl. No.: 16/456,175

(22) Filed: Jun. 28, 2019

(65) Prior Publication Data

US 2019/0320273 A1 Oct. 17, 2019

Related U.S. Application Data

(63) Continuation of application No. 15/591,535, filed on May 10, 2017, now Pat. No. 10,419,860.

(51) Int. Cl.
*H04R 25/00* (2006.01)
*H04R 17/00* (2006.01)
(Continued)

(52) U.S. Cl.
CPC ......... *H04R 25/604* (2013.01); *A61F 2/1602* (2013.01); *H04R 17/00* (2013.01);
(Continued)

(58) Field of Classification Search
CPC .... H04R 25/604; H04R 25/554; H04R 17/00; H04R 25/00; H04R 25/552; A61F 2/1602; A61F 9/0008; A61N 1/36; A61B 3/125
See application file for complete search history.

(56) References Cited

U.S. PATENT DOCUMENTS

| 4,051,455 | A | | 9/1977 | Fowler et al. |
| 4,922,913 | A | * | 5/1990 | Waters, Jr. ............... A61B 3/16 |
| | | | | 600/398 |

(Continued)

FOREIGN PATENT DOCUMENTS

WO 2015081298 A1 6/2015

OTHER PUBLICATIONS

Karen Kloosterman, Bionic contact lenses turn touch into vision, http://www.israel21c.org/bionic-contact-lenses-turn-touch-into-vision, Jul. 23, 2013 (last visited May 9, 2017).

(Continued)

*Primary Examiner* — Oyesola C Ojo
(74) *Attorney, Agent, or Firm* — Cantor Colburn LLP; Kristofer Haggerty

(57) ABSTRACT

Embodiments of the present invention are directed to a method of stimulating a cornea. A non-limiting example of the method includes capturing a sound with a microphone. A non-limiting example of the method also includes transducing the sound to an electric signal by a microprocessor. A non-limiting example of the method also includes stimulating a piezo-electric element adjacent to a receptor of the cornea, wherein the piezo-electric element is positioned on an eye lens with an electric signal. A non-limiting example of the method also includes mechanically stimulating a receptor of the cornea with the stimulated piezo-electric element.

20 Claims, 17 Drawing Sheets

(51) Int. Cl.
  *A61F 2/16*     (2006.01)
  *A61F 9/00*     (2006.01)
  *A61B 3/125*    (2006.01)
  *A61N 1/36*     (2006.01)

(52) U.S. Cl.
  CPC ............ *H04R 25/554* (2013.01); *A61B 3/125* (2013.01); *A61F 9/0008* (2013.01); *A61N 1/36* (2013.01); *H04R 25/00* (2013.01); *H04R 25/552* (2013.01)

(56) References Cited

U.S. PATENT DOCUMENTS

| | | | | |
|---|---|---|---|---|
| 5,109,852 A | * | 5/1992 | Kaye | A61B 3/16 600/398 |
| 6,312,393 B1 | * | 11/2001 | Abreu | A61B 3/1241 600/558 |
| 6,673,014 B2 | | 1/2004 | Badehi et al. | |
| 7,321,795 B2 | * | 1/2008 | Bogdanowicz | A61N 1/32 351/159.02 |
| 8,172,769 B2 | * | 5/2012 | Lenhardt | A61B 8/0808 600/561 |
| 8,506,473 B2 | | 8/2013 | Puria | |
| 8,778,022 B2 | * | 7/2014 | Blum | H02J 50/10 623/6.22 |
| 8,820,934 B1 | * | 9/2014 | Ho | G02C 7/04 351/219 |
| 8,870,370 B1 | * | 10/2014 | Otis | A61B 5/14532 351/159.03 |
| 9,185,486 B2 | * | 11/2015 | Pugh | G02C 7/04 |
| 9,199,081 B2 | * | 12/2015 | Zalevsky | A61N 1/36046 |
| 9,271,677 B2 | * | 3/2016 | Leonardi | A61B 3/16 |
| 9,630,007 B2 | | 4/2017 | Kulah et al. | |
| 10,025,118 B1 | * | 7/2018 | Markus | G02C 7/04 |
| 2002/0123671 A1 | | 9/2002 | Haaland | |
| 2004/0179268 A1 | | 9/2004 | Barbastathis | |
| 2011/0158444 A1 | * | 6/2011 | Waldmann | H04R 25/604 381/326 |
| 2012/0041499 A1 | * | 2/2012 | Towe | A61N 1/32 607/3 |
| 2012/0286765 A1 | * | 11/2012 | Heuvel | H04R 25/606 324/76.49 |
| 2014/0187155 A1 | * | 7/2014 | Siegumfeldt | H04B 5/0062 455/41.1 |
| 2014/0243645 A1 | | 8/2014 | Leonardi | |
| 2015/0133055 A1 | | 5/2015 | Choi et al. | |
| 2017/0087014 A1 | | 3/2017 | Potter, Jr. et al. | |
| 2018/0133055 A1 | * | 5/2018 | Lopath | A61F 9/008 |
| 2018/0149884 A1 | * | 5/2018 | Miller | G02B 27/017 |
| 2018/0161579 A1 | * | 6/2018 | Franke | A61B 5/389 |
| 2018/0332409 A1 | | 11/2018 | Cahan et al. | |
| 2018/0332410 A1 | | 11/2018 | Cahan et al. | |

OTHER PUBLICATIONS

List of IBM Patents or Patent Applications Treated as Related (Appendix P); Date Filed Jun. 28, 2019, 2 pages.

* cited by examiner

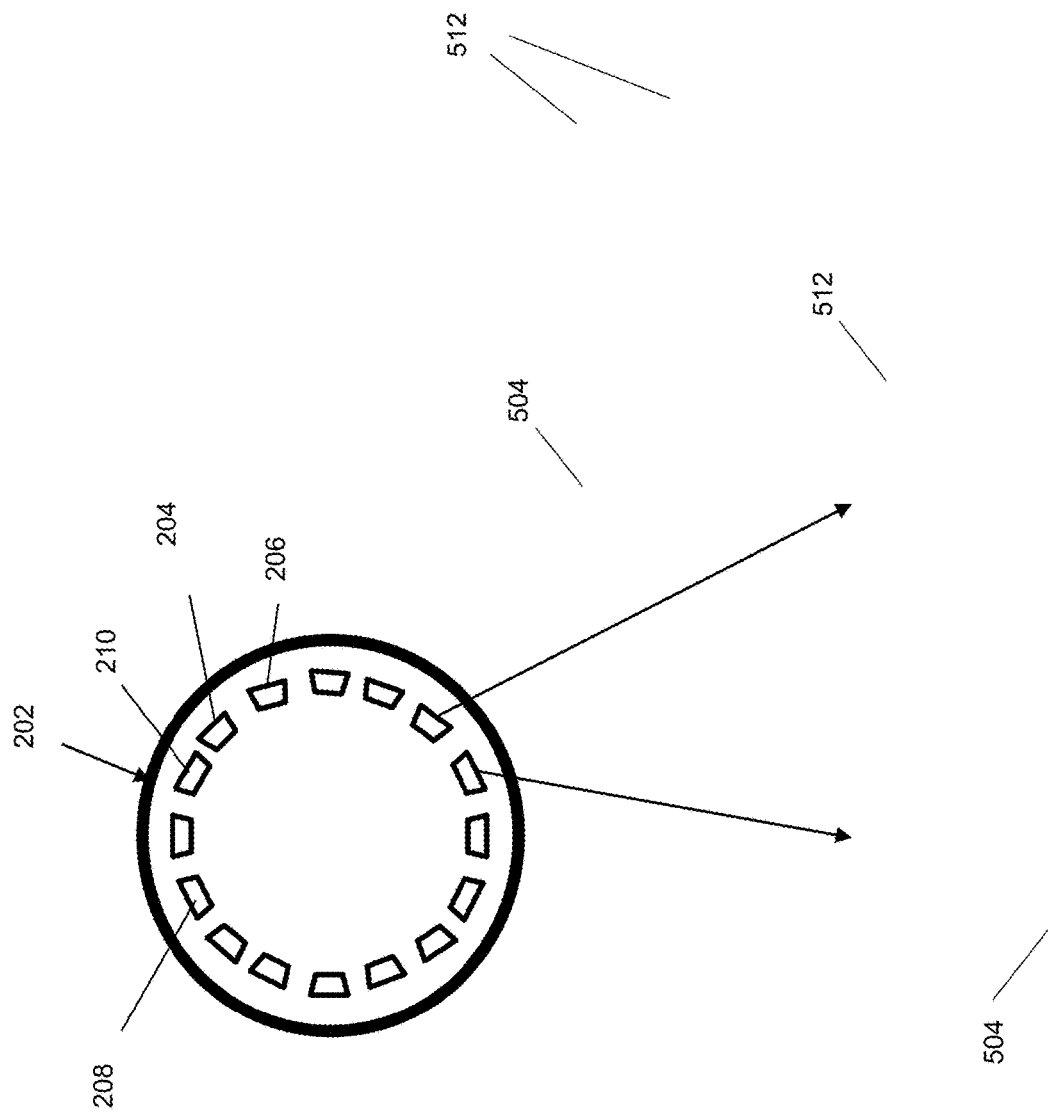

EYE-MOUNTED HEARING AID

DOMESTIC PRIORITY

This application is a continuation of U.S. application Ser. No. 15/591,535, filed May 10, 2017, the contents of which are incorporated by reference herein in its entirety.

BACKGROUND

The present invention generally relates to hearing aids and, more specifically, relates to eye-mounted hearing aids.

Individuals with profound deafness or severe to profound hearing loss can find it difficult or impossible to understand and interpret sound, even with amplification. Individuals with severe or profound deafness can be reliant upon lip reading or sign language and, in some instances, can use cochlear implants to overcome their hearing impairments. Cochlear implants are surgically implantable devices that bypass much of the peripheral auditory system, including the outer, middle, and inner ear, and interact directly with the central auditory system. Such implants can detect sound through a microphone appended outside of the ear, convert the sound into patterns of electrical pulses, and transmit those pulses to electrodes in the cochlea where an auditory nerve can detect the signals.

When the auditory nerve transmits the detected signals to the brain, the brain can recognize the signals as sound. Thus, cochlear implants can enable persons that are naturally unable to hear to perceive and understand sound. However, cochlear implants can be costly and invasive. For example, cochlear implants, by design, include components internal and external to the ear and, thus, can involve surgical implantation.

Non-invasive hearing aids can in some instances be preferred over surgically implanted devices because they can provide more comfort and less risk of adverse outcomes to a user. Moreover, avoiding surgery can reduce costs associated with treatment.

The cornea of the eye is a highly sensitive area of the body. The cornea contains a high density of mechanoreceptors that can transmit signals to the brain when, for example, the receptors detect contact of a surface the eye or a change in the nature of contact with the surface of the eye.

SUMMARY

Embodiments of the present invention are directed to a system for stimulating the cornea. A non-limiting example of the system includes an eye lens. The non-limiting example also includes a plurality of piezo elements positioned upon the eye lens. The non-limiting example also includes a power supply in electrical communication with the plurality of piezo elements. Such embodiments can provide a non-invasive system for transmitting sound information to the brain through receptors of the cornea.

Embodiments of the present invention are directed to a method of stimulating a cornea. A non-limiting example of the method includes capturing a sound with a microphone. A non-limiting example of the method also includes transducing the sound to an electric signal by a microprocessor. A non-limiting example of the method also includes stimulating a piezo-electric element adjacent to a receptor of the cornea, wherein the piezo-electric element is positioned on an eye lens with an electric signal. A non-limiting example of the method also includes mechanically stimulating a receptor of the cornea with the stimulated piezo-electric element. Such embodiments can provide methods of transmitting sound to the brain without surgical intervention, for instance in individuals with severe hearing impairments.

Embodiments of the present invention are directed to a method of treating a hearing impairment. A non-limiting example of the method includes placing an eye lens comprising a piezo electric element upon a cornea of a patient. A non-limiting example of the method also selectively activating the piezo electric element based at least in part upon the sound. A non-limiting example of the method also stimulating a cornea receptor with the activated piezo electric element. A non-limiting example of the method also includes transmitting a signal to a brain of the patient by the stimulated cornea receptor.

Embodiments of the present invention are directed to a system for stimulating the cornea. A non-limiting example of the system includes an eye lens including a plurality of piezo elements, a first microcontroller in communication with the piezo elements, a near field communication (NFC) tag in communication with the first microcontroller, and an antenna in communication with the NFC tag. A non-limiting example of the system also includes an external device including an NFC reader, a second microcontroller in communication with the NFC reader, and memory in communication with the second microcontroller. A non-limiting example of the system also includes a microphone in communication with the piezo elements. Such embodiments can advantageously provide a system for transmitting sound information to the brain with a relatively light-weight contact lens.

Embodiments of the present invention are directed to a method of treating a hearing impairment. A non-limiting example of the method includes converting a sound including a plurality of frequencies to a plurality of mechanical signals. A non-limiting example of the method also includes stimulating a plurality of mechanoreceptors of a cornea with the plurality of mechanical signals in a pattern reflective of the plurality of frequencies. Such embodiments can advantageously leverage the high sensitivity of the eye and provide sound information to the brain while bypassing the conventional auditory system for hearing impaired individuals.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIGS. 7A-7C depict an eye-based hearing system according to one or more embodiments of the present invention.

Figure 1:
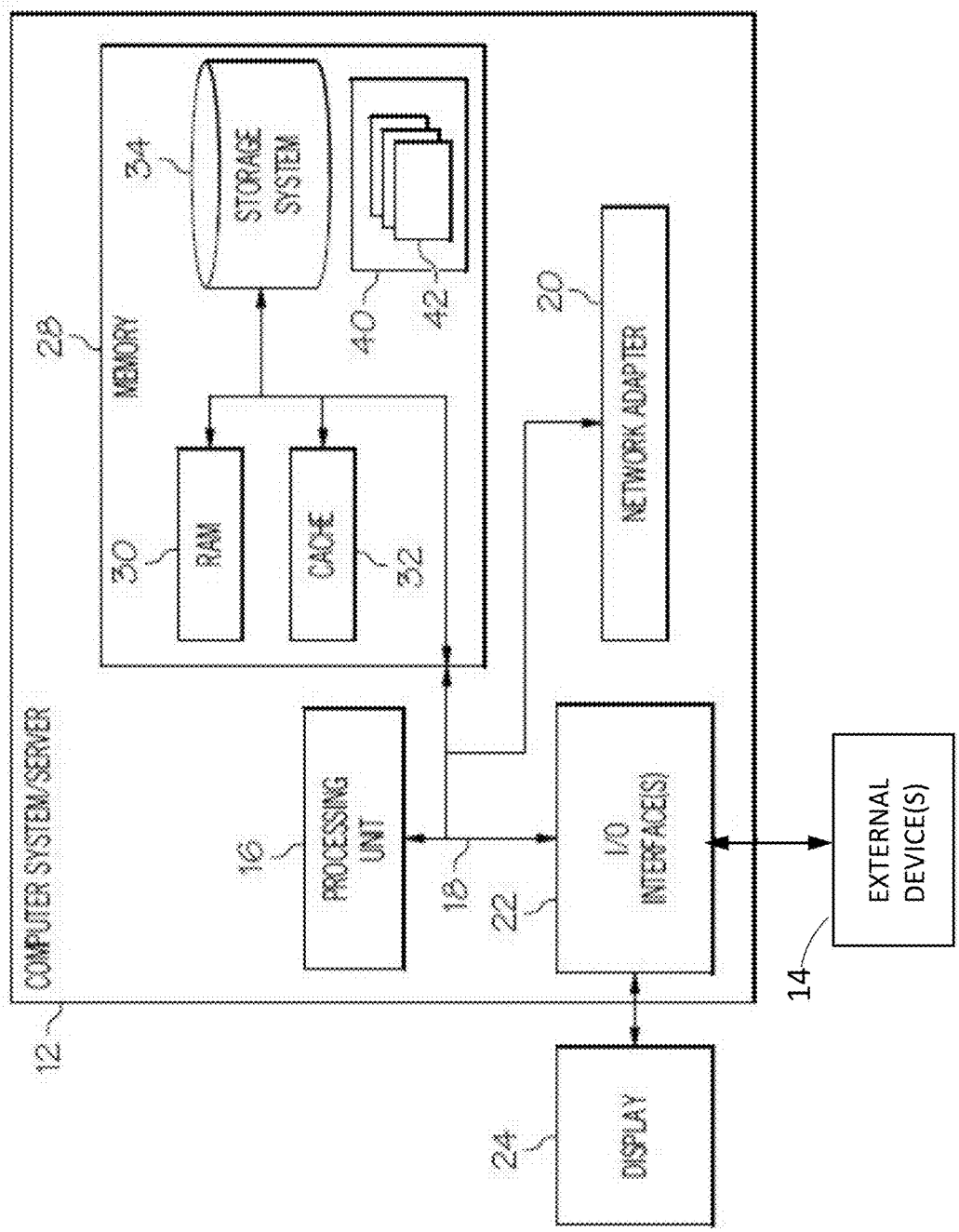
FIG. 1 depicts a computer system according to one or more embodiments of the present invention.

In the accompanying figures and following detailed description of the embodiments of the invention, the various elements illustrated in the figures are provided with two or three digit reference numbers. With minor exceptions, the leftmost digit(s) of each reference number correspond to the figure in which its element is first illustrated.

DETAILED DESCRIPTION

Hearing impairments can range in severity from minor impairments resulting in difficulty in hearing to total deafness. Those with moderate deafness can rely upon a hearing aid to assist with understanding speech, while those with severe hearing loss and profound deafness can rely upon surgically implanted devices, in some cases, or might need to resort to lip reading and/or sign language.

Cochlear implants can be used to provide a sense of sound to a person that is profoundly deaf or severely hard of hearing in both ears. Cochlear implants bypass most of the peripheral auditory system and, thus, require surgical implantation. The cochlear implants can receive sound and convert that sound to mechanical movement of hair cells or electrical pulses of electrodes in the cochlea. The brain can recognize these signals as auditory.

Embodiments of the invention can aid individuals with hearing impairments of any severity, including total deafness, to understand speech by providing an eye-based hearing aid. Systems and methods according to embodiments of the invention include an eye-mounted lens including elements that can convert auditory signals to mechanical stimulation of the cornea.

The above-described aspects of the invention address the shortcomings of the prior art by providing a non-invasive method of aiding in hearing for individuals with hearing impairments. An eye-mounted lens can include elements that press onto surfaces of the eye, in particular surfaces of the cornea, to help the brain decipher through touch what the wearer is hearing. The cornea is the front part of the eye that covers the iris, pupil and anterior chamber and also contains a high density of nerve endings, rendering it highly sensitive to touch. This sensitivity can allow, for example, selective stimulation of different regions of the cornea corresponding to different frequencies, amplitudes, or other sound characteristics, which can in turn provide an alternate mechanism for the brain to interpret sound in hearing impaired individuals. For example, as the wearer continues to receive mechanical stimulation in particular regions of the cornea in response to particular frequencies, the brain can learn to decipher those mechanical signals as sound and allow the wearer to interpret auditory signals.

The mechanical signals can be imparted to the wearer by piezo elements embedded in a contact lens-like structure, also referred to herein as an eye lens. Auditory signals can be captured by a microphone that innervates mechanical receptors in different areas of the cornea based upon sound frequency. For example, in some embodiments of the invention, auditory signals captured by a microphone, for example a microphone included within the lens, are transduced to vibration of small piezo elements, each with a different resonance frequency.

FIG. 1 depicts a computing system node 100 according to one or more embodiments of the present invention. Computer system/server 12 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
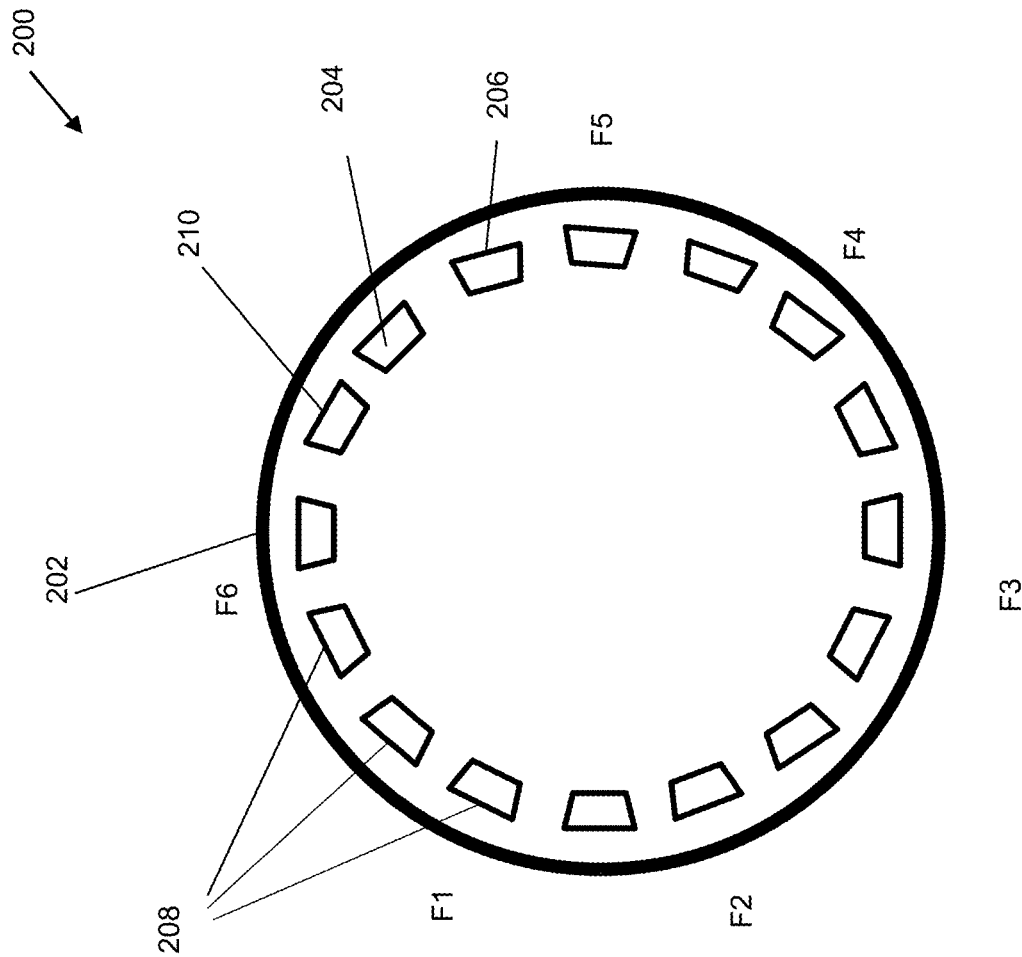
FIG. 2 depicts an eye-based hearing system according to one or more embodiments of the present invention.

Turning now to a more detailed description of aspects of the present invention, FIG. 2 depicts an eye-based hearing system 200 according to some embodiments of the invention. The system 200 includes a lens 202 that can be positioned over the cornea of a user. The eye lens 202 can be a contact lens or similar transparent, flexible material suitable for wear on the eye, and can include a plurality of devices and components. The lens 202 can include a microcontroller 204. The microcontroller can be in communication with a microphone 206 and a plurality of piezo elements 208. The lens 202 can also include a power supply 210, such as a micro- or nano-battery. The components can be positioned in different areas of the lens 202 to stimulate different areas of the cornea upon receipt of an auditory signal. For example, the piezo elements 208, microphone 206, and/or microcontroller 204 can be positioned so as to form a ring near to the circumference of the lens 202, leaving the center of the lens free of components so as to not obstruct the view of a wearer. In operation, the microphone 206 can receive an auditory signal and, in communication with the microcontroller, the system 200 can process that signal to determine one or more frequencies associated with the auditory signal and selectively activate one or more piezo elements 208. In some embodiments of the invention, different piezo elements 208 are associated with and respond to different frequencies (for instance, frequencies that vary based upon location on the cornea, such as F1, F2, F3, F4, F5, F6, as illustrated).

The piezo elements 208 can include a piezoelectric ceramic or crystal placed between two metal plates. Piezoelectric ceramic or crystal materials are known and include, for example, quartz, lead zirconate titanate (PZT), barium titanate, and lithium niobate. In some embodiments of the invention, the piezo elements 208 include PZT. A voltage applied to the piezoelectric material can change the shape of the material by a small amount (i.e., up to a 4% change in volume). An input voltage can be applied cross a short length of a bar of piezo material, for instance a piezo ceramic material such as PZT, creating an alternating stress in the bar by the inverse piezoelectric effect and causing the bar to vibrate. The vibration frequency can be selected to be the resonant frequency of the block. In some embodiments of the invention, the vibration frequency of the piezo elements 208 ranges from 1 Herz (Hz) to 100 kilohertz (kHz).

In some embodiments of the invention, a microphone 206 is included on the lens 202. In such embodiments, the microphone 206 can have dimensions of less than or equal to 1 millimeter squared and a thickness of less than or equal to 1 millimeter (mm). For instance, the microphone 206 can be a MEMS (microelectro-mechanical systems) microphone having a length and width, for example, of each less than or equal to 1.0 mm, or less than or equal to 0.84 mm and a thickness on the order of several hundred microns.

Figure 3:
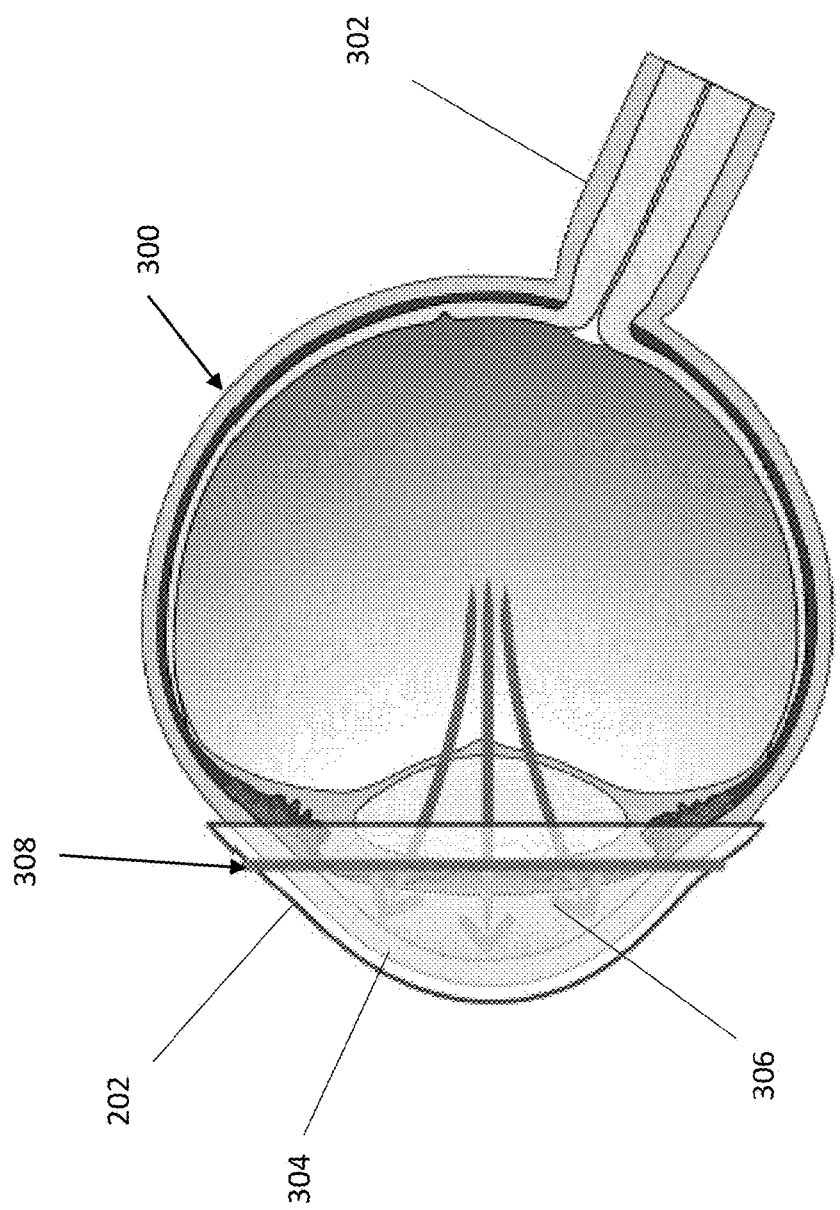
FIG. 3 depicts an eye-based hearing system according to one or more embodiments of the present invention.

FIG. 3 illustrates the placement of the eye-based hearing system of FIG. 2 upon the eye 300. The eye 300 includes an optic nerve 302 and a cornea 304. A lens 202 including a plurality of components in a ring 308 near the periphery of the lens 202 can be place over the cornea 304. The ring of components 308 can be positioned around the exterior of the lens 202 such as to provide an unobstructed path 306 for light to enter into the eye, allowing the wearer to have minimal visual disruption.

Figure 4:
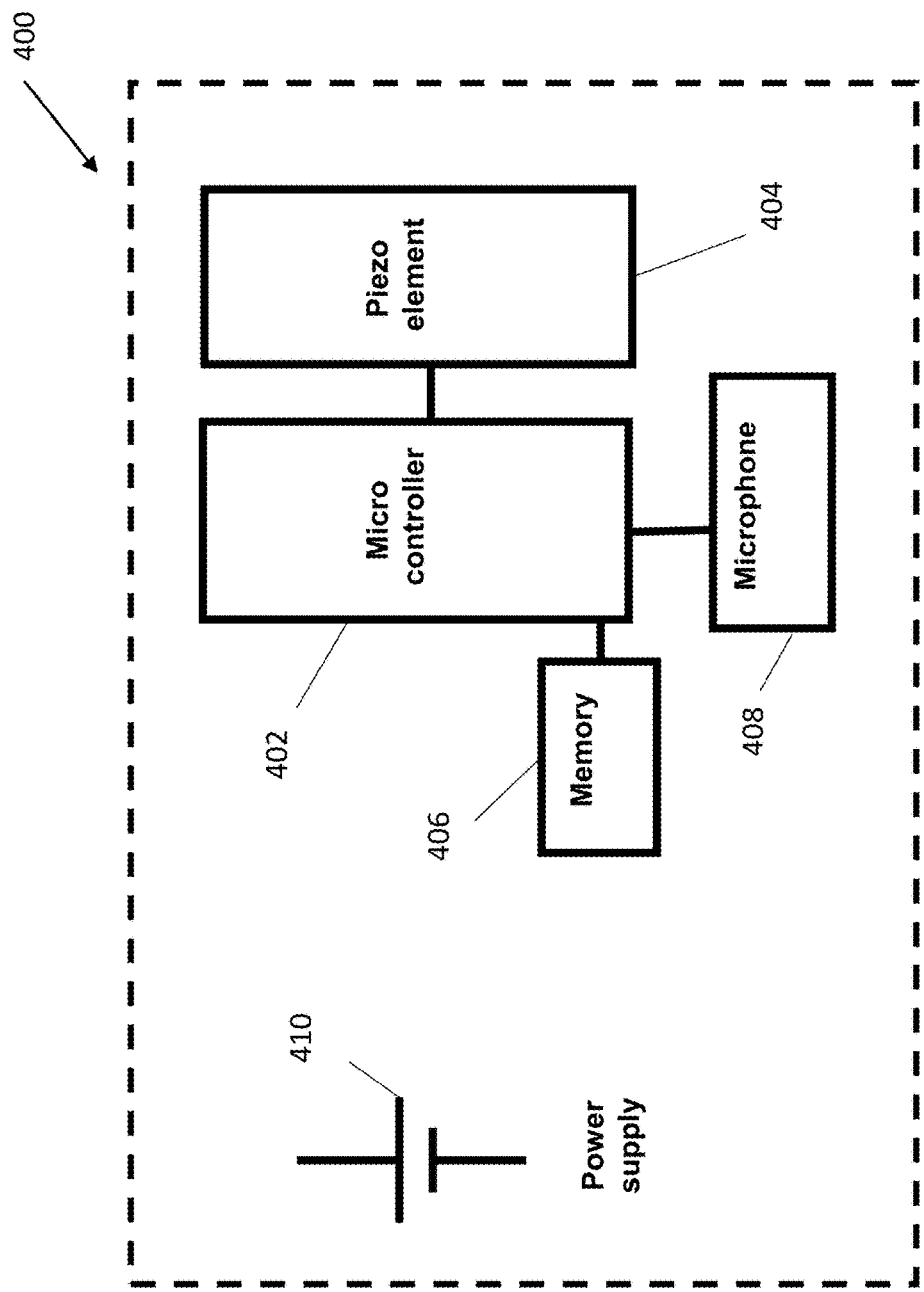
FIG. 4 depicts an eye-based hearing system according to one or more embodiments of the present invention.

FIG. 4 depicts a schematic of an eye-based hearing system 400 according to one or more embodiments of the present invention. As is shown, the system 400 includes a microcontroller 402. The microcontroller can be connected to a microphone 408 and a piezo element 404. The microcontroller 402 can also be connected to a memory component 406. The system 400 can also include a power supply 410.

Figure 5A:
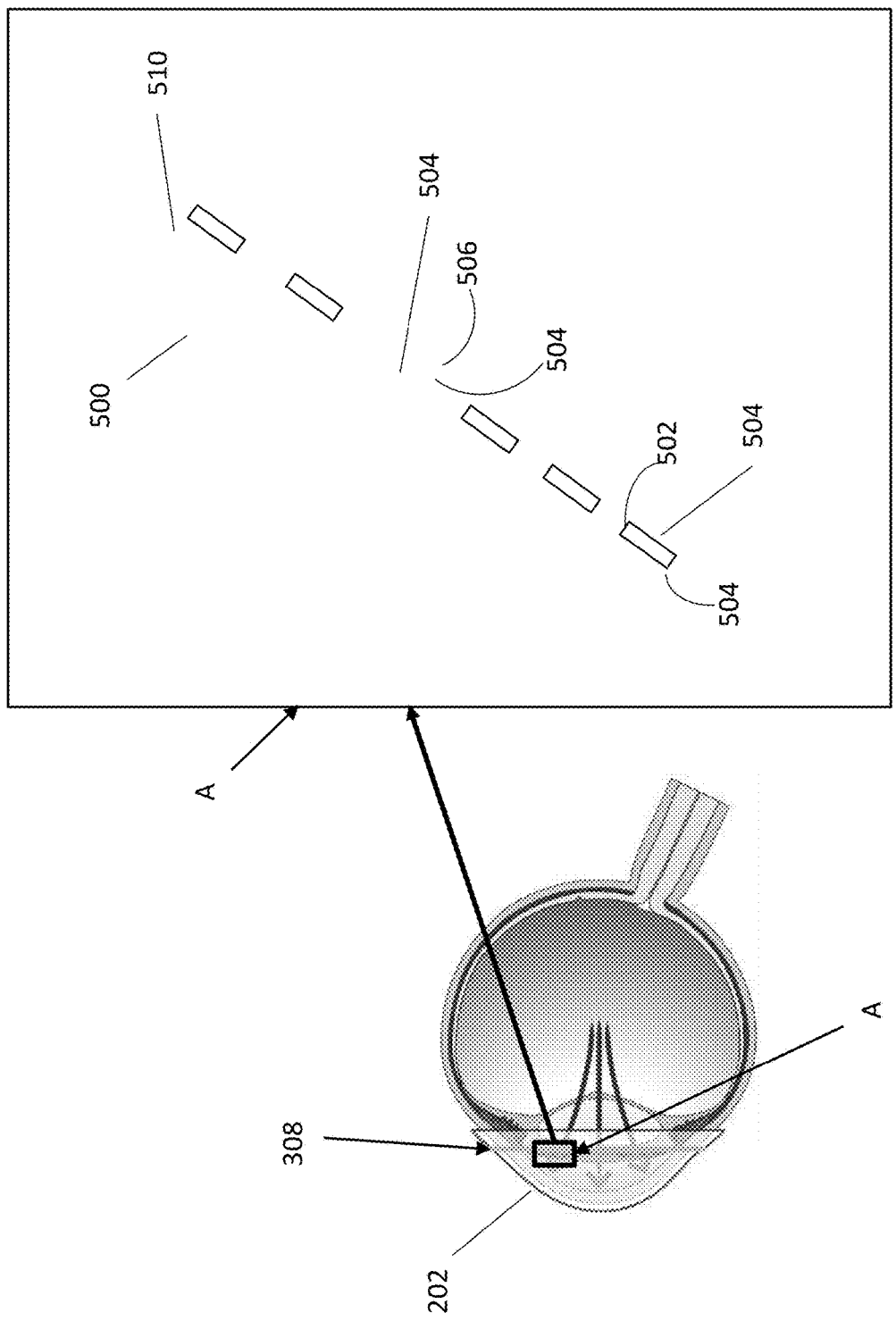
FIG. 5A depicts an eye-based hearing system according to one or more embodiments of the present invention.

FIG. 5A depicts an eye-based hearing system according to one or more embodiments of the present invention illustrating an exemplary organization of piezo elements on a lens 202. The ring of components 308 can include a substrate 500 and one or more electrodes 504. A plurality of piezo elements, for instance in the form of small rods or hair like structures (piezo rods) or discs formed of piezoelectric material 502, 506 can be positioned on a substrate 500. The piezo elements 502, 506 can be in a relaxed state 502 or a stimulated state 506. The piezo elements can be associated with electrodes 504, including in a configuration in which one electrode 504 is adjacent to a first surface of the piezo element 502, 506, and a second electrode 504 is adjacent to a second surface of the piezo element 502, 506. In some embodiments of the invention, the piezo element in the form of a rod 502 is optionally elevated off of the surface of a substrate 500 by an additional layer 510. As is illustrated, piezo rods in a stimulated state 506 can bend toward (shown) the surface of the eye or away from the surface of the eye (not shown). A voltage can be sent to each individual piezo rod 502, 506 through one or more electrodes 504 through one or more wires or electrical conduits (not shown). The piezo rods 502, 506 can be selectively stimulated based upon location on the ring of components 308, or can be selectively stimulated by applying a variable voltage. The piezo rods, when stimulated, can exhibit a motion sufficient to selectively stimulate a region of the cornea. The stimulated piezo rods 506, for example, can bend, contract, pulse, vibrate, or include a variable motion based at least in part upon the auditory signal received by the microphone.

Figure 5B:
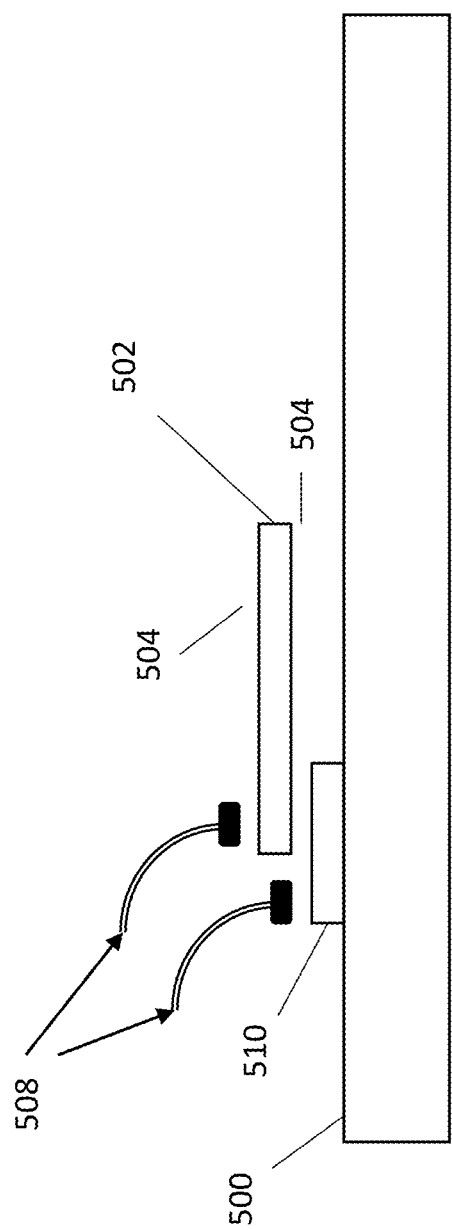
FIG. 5B depicts an eye-based hearing system according to one or more embodiments of the present invention.

FIG. 5B depicts an exemplary piezo element according to some embodiments of the invention. A piezo element in the form of a small rod 502 can be positioned in between two electrodes 504. The electrodes 504 can be associated with one or more wires 508 to provide electrical communication with a power source or other components of an eye-based hearing system. In some embodiments of the invention, the piezo element in the form of a rod 502 is elevated off of the surface of a substrate 500 by an additional layer 510. The additional layer 510 can include, for example, a raised portion of a substrate, a second layer of substrate, a buried oxide layer, or other material sufficient to mechanically support the piezo element 502 and electrodes 504. In some embodiments, not shown in FIG. 5B, the piezo element 502 and one or more of the associated electrodes 504 are adjacent to the substrate 500 such that no gap is present between the piezo element and the substrate 500. The substrate 500 can include any material suitable for contact lens structures or that can be appended to an eye lens material. For example, the substrate 500 can include silicon based materials, such as a silicon on insulator (SOI), or aluminum based materials. In some embodiments, the substrate is composed of biocompatible materials. Electrodes 504 can include any suitable conductive material, such as platinum, titanium, gold, and mixtures and alloys thereof. In some embodiments, as is shown in FIG. 5B for instance, a piezo element 502 can be in a unimorphic configuration.

Figure 6:
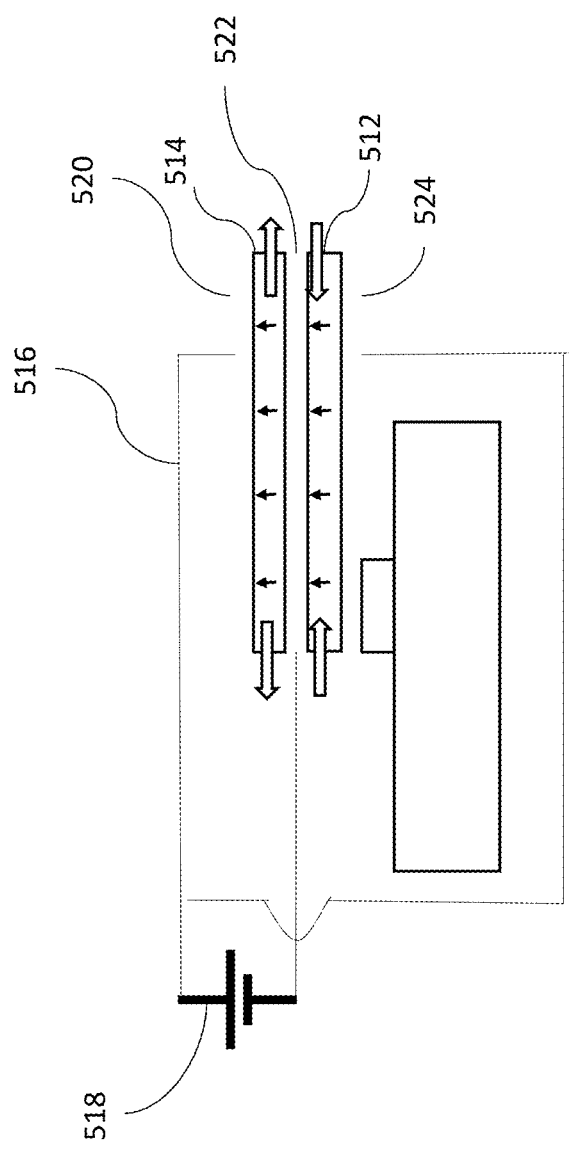
FIG. 6 depicts an eye-based hearing system according to one or more embodiments of the present invention.

FIG. 6 depicts another exemplary piezo element according to some embodiments of the invention. As is shown in FIG. 6, in some embodiments, the piezo element can be in a bimorph configuration, such as a bimorph configuration configured to provide parallel actuation. As is shown, a structure can include a lower piezo structure 512 and an upper piezo structure 514. The lower piezo structure and upper piezo structure can be in contact with a plurality of electrodes, such as a bottom electrode 524 in contact with the lower piezo structure 512, a middle electrode 522 in contact with the lower piezo structure 512 and the upper piezo structure 514, and a top electrode 520 in contact with the upper piezo structure 514. The electrodes can be connected to a power supply 518. The polarization, as is illustrated in FIG. 6, can be in the upward direction in both the lower piezo structure 512 and the upper piezo structure 514. In some embodiments of the invention, upon activation, the lower piezo structure 512 can experience a generative stress in an inward direction on one piezo structure, such as the lower piezo structure 512, and an outward direction on the other piezo structure, such as the upper piezo structure 514, as indicated by horizontal arrows in FIG. 6. Other electric configurations can also be used.

Figure 7C:
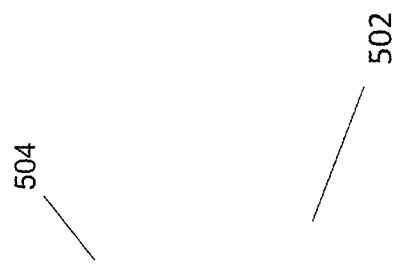
Figure 7B:
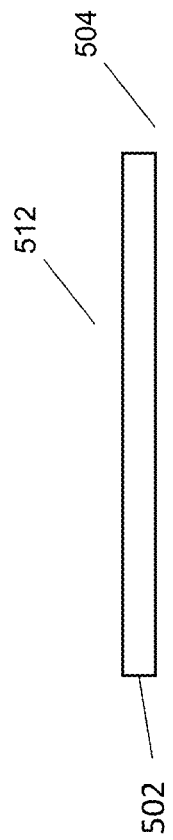

FIG. 7A depicts an eye-based hearing system according to one or more embodiments of the present invention illustrating another exemplary organization of piezo elements on a lens 202. The piezo elements (not visible) can be circular in shape, for example, and can be positioned adjacent to a first electrode 504 and a second electrode 512. The piezo elements can be unimorphic or bimorphic. In some embodiments, the piezo elements are bimorphic. FIG. 7B depicts a side view of an exemplary piezo element 502 of FIG. 7A positioned between electrodes 504 and 512. FIG. 7C depicts a cut away top view of the exemplary piezo element 502 of FIGS. 7A and 7B.

Although FIGS. 7B and 7C illustrate a system in which the piezo element is in contact with electrodes along an entire surface of the piezo element, in some embodiments, one or more cavities is positioned between the piezo element and the electrodes. For example, in some embodiments of the invention, one or more electrodes contact the piezo element at an outer edge along a circumference but not in a central region. For example, a cavity can enable an outward pressure of an electrode adjacent the cavity upon contraction of the piezoelectric material.

Figure 8A:
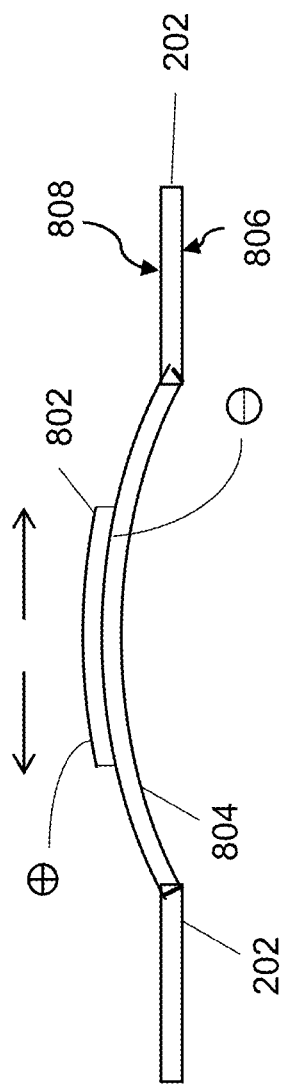
FIGS. 8A-8C depict an eye-based hearing system according to one or more embodiments of the present invention.
Figure 8B:
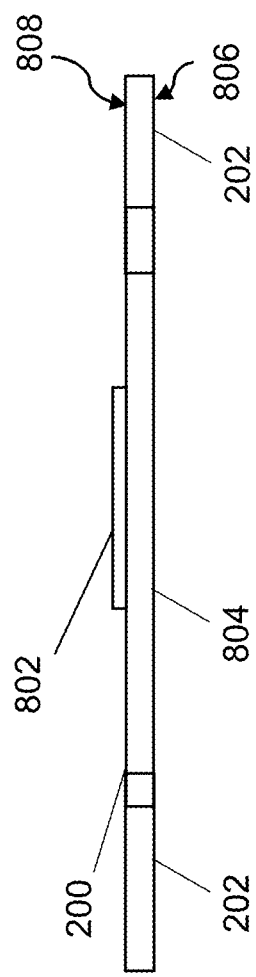
Figure 8C:
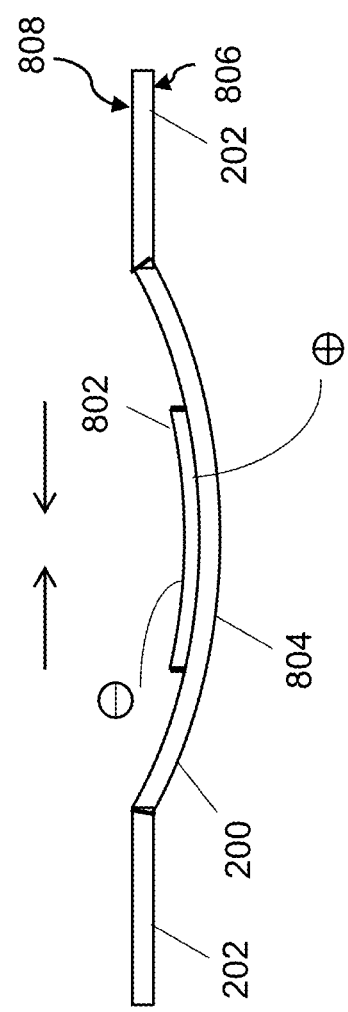

FIGS. 8A-8C illustrate an exemplary motion of a piezo structure 802 upon activation. The piezo structure 802 can be mounted on a substrate 804 that is flexible and capable of vibrating upon stimulation of the piezo structure 802, such as a thin polymeric material including, for instance, polysilicon materials, SOI, or PDMS. In some embodiments, the substrate 804 is a biocompatible material. For example, in some embodiments the substrate 804 is substantially free or free of metals. The substrate 804 can be in contact with the eye lens 202. The eye lens 202 includes a top surface 808 and a bottom surface 806, such that the bottom surface 806 can be applied to the surface of an eye (not shown in FIG. 8A-8C). As is shown in FIG. 8A, application of a positive voltage to a surface of the piezo structure 802 opposite the lens structure 202 can result in an expansion of the piezo structure 802 and accompanying distortion of the substrate 804 away from the surface of an eye. FIG. 8B illustrates the system of FIG. 8A wherein the piezo structure 802 is in a relaxed state and no voltage is applied. FIG. 8C illustrates the piezo structure 802 of FIG. 8A with voltages of opposite polarity and illustrates contraction of the piezo structure 802 and resultant distortion of the substrate 804 toward the surface of an eye.

Figure 9:
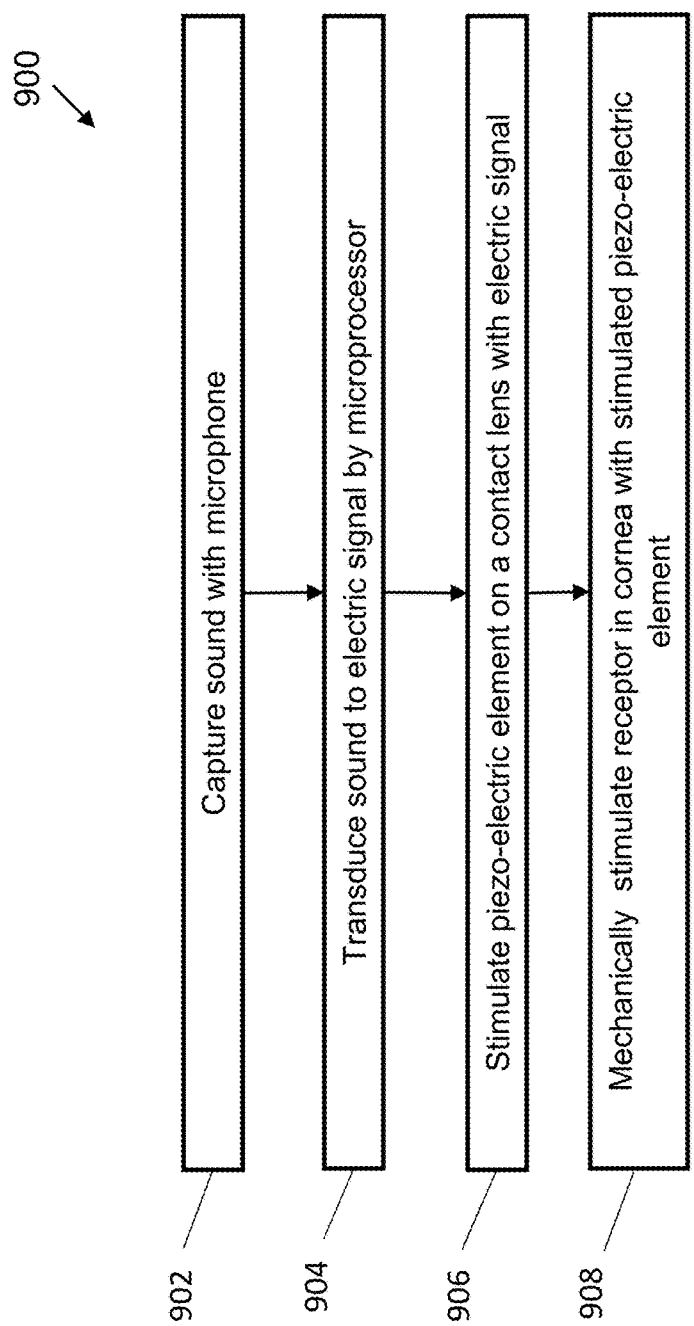
FIG. 9 depicts a flow diagram illustrating a method according to one or more embodiments of the present invention.

FIG. 9 depicts a flow diagram illustrating a method of transforming auditory signals 900 according to one or more embodiments of the present invention. The method 900 can include capturing sound with a microphone, as shown at block 902. In some embodiments, the microphone is positioned on a flexible transparent lens placed upon a cornea. In some embodiments, the microphone is positioned on a device external to a flexible transparent lens, such as on eyeglasses or an adhesive material worn by a user of the lens. The method 900 also includes transducing the sound to an electric signal or a plurality of electric signals by a microprocessor, as shown at block 904. The method 900 also includes stimulating a piezo-electric element on an eye lens with the electric signal(s), as shown at block 906.

In some embodiments of the invention, a plurality of piezo-electric elements are provided on an eye lens, each responding to a different frequency. In some embodiments of the invention, the piezo-electric elements are stimulated based upon resonance frequency. In some embodiments of the invention, a piezo-electric element serves as a channel and can translate sound frequency to vibration frequency within a frequency range. In some embodiments of the invention, the piezo-electric elements are stimulated to vibrate at a frequency corresponding to a frequency of the related to a frequency of the sound. The method 900 also includes mechanically stimulating a receptor in the cornea with a stimulated piezo-electric element, as shown at block 908. In some embodiments of the invention, a stimulated receptor in the cornea transmits a signal to the brain that can be interpreted by the brain in accordance with the sound.

In some embodiments of the invention, power is supplied to the piezo elements and microcontroller of a system by an integrated power supply, such as a battery, positioned on an eye lens. In some embodiments of the invention, power is supplied to the microcontroller and piezo elements by an external source. For example, in some embodiments power and other functionalities can be transmitted to components on an eye lens by NFC with an external component. For example, NFC components can be integrated into eyeglasses that are near the eye lens and can transmit power. Alternatively, another material that can be positioned in proximity to the eye lens can be used to transmit power, such as a nose clip, or an adhesive. In some embodiments of the invention, energy harnessed by eyelid movement is transmitted to the system.

In some embodiments of the invention, a system includes one or more external devices. External devices included within the system include devices external to an eye lens, such as glasses, nose clips, ear buds, tablets, computers, smartphones, smart watches, etc. For example, in some embodiments, a system includes two external devices, for instance a first external device including eye glasses, and a second external device including a smartphone.

In some embodiments of the invention, data can be transmitted to components on an eye lens by RF such as Bluetooth with an external component. For example, in an embodiment, an eye lens includes a battery and an RF receiver and an external device, such as eye glasses, includes an RF transmitter and microphone. In such an embodiment, for example, the external device can transmit data to the eye lens through RF transmission, for instance via a Bluetooth transmission.

Figure 10:
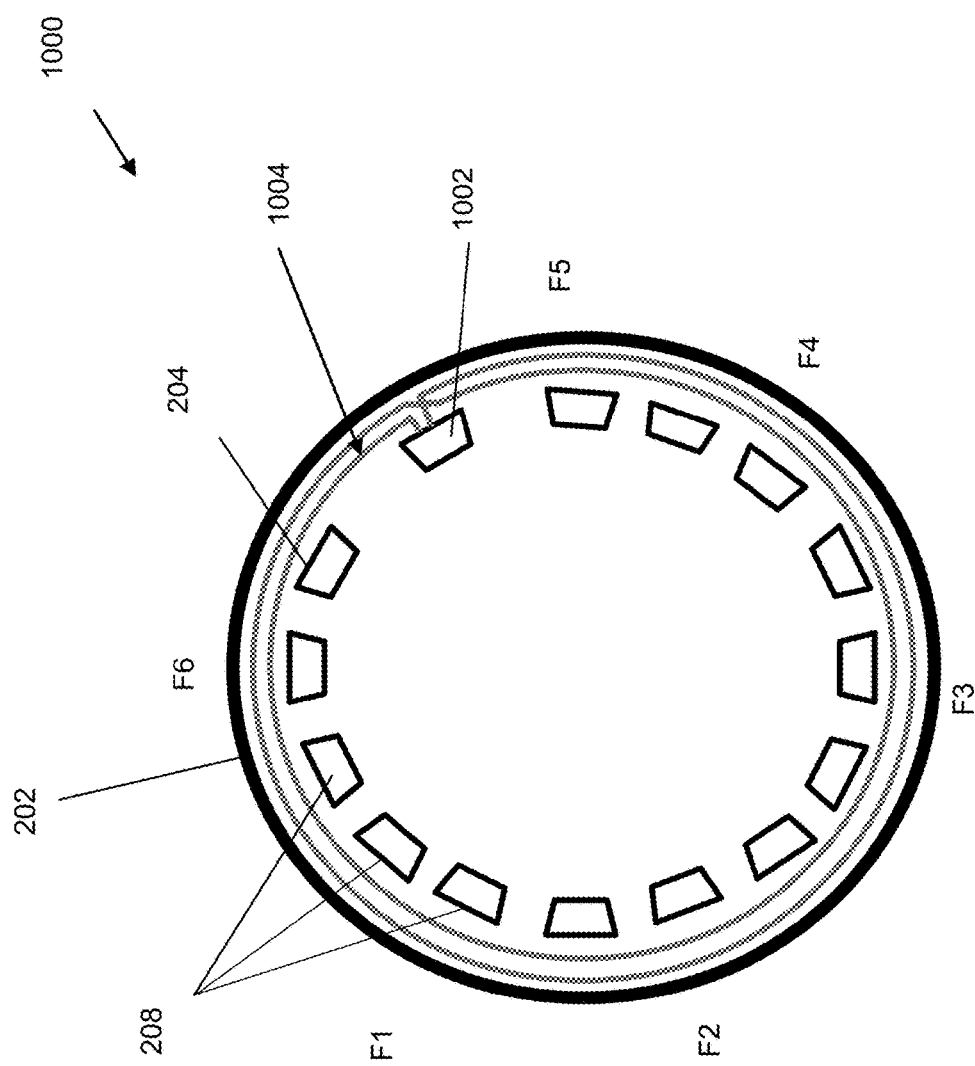
FIG. 10 depicts an eye-based hearing system according to one or more embodiments of the present invention.

FIG. 10 depicts an eye-based hearing system 1000 according to one or more embodiments of the present invention, wherein the lens does not include an integrated power supply. As is shown, the system 100 includes an eye lens 202. Upon the lens are a plurality of components, including a microcontroller 204 and a plurality of piezo elements 208. The system 1000 can include an antenna 1004 and an integrated circuit (IC) tag 1002, for example, for transmission of power by NFC.

Figure 11:
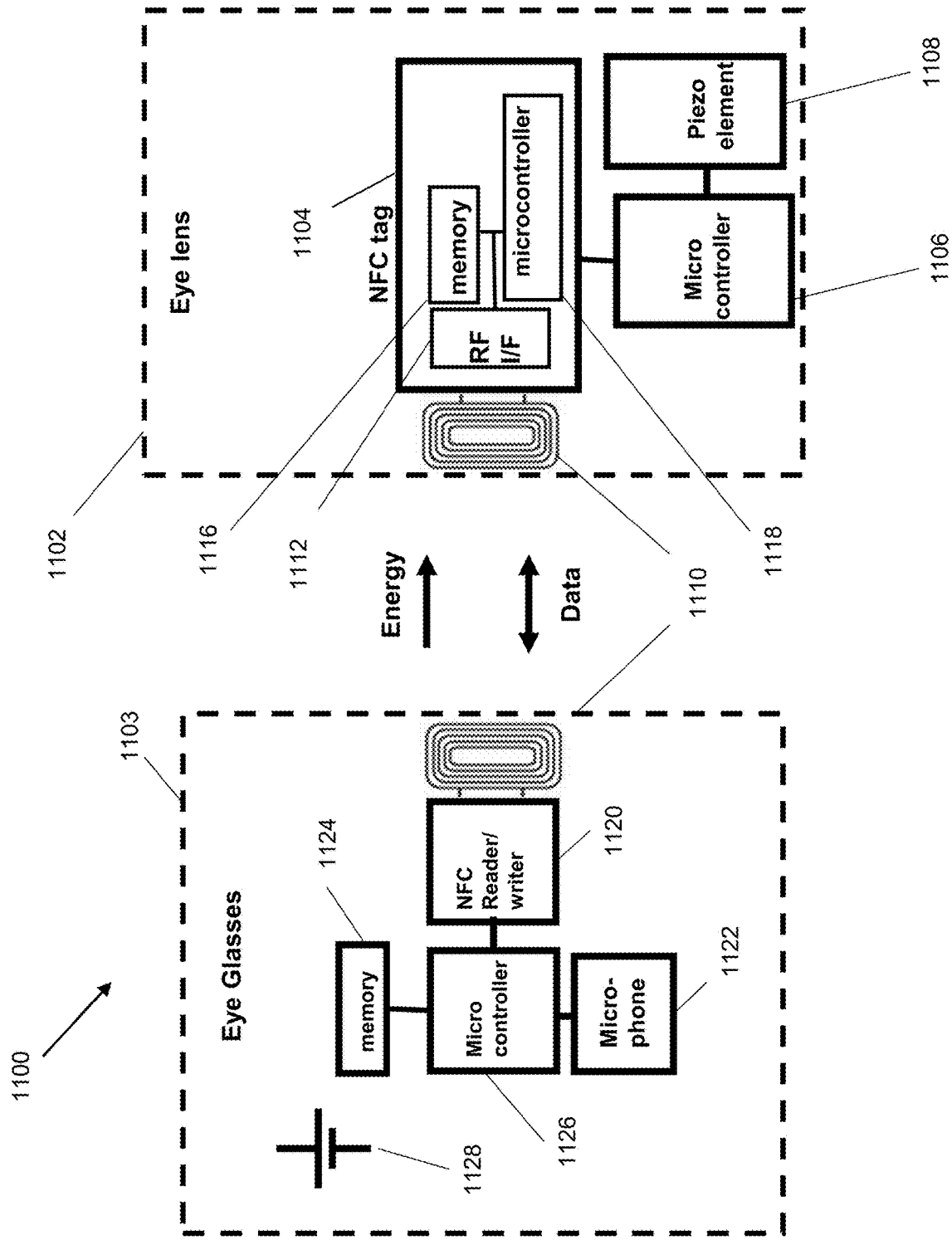
FIG. 11 depicts an eye-based hearing system according to one or more embodiments of the present invention.

FIG. 11 depicts a schematic of an eye-based hearing system according to one or more embodiments of the invention. As is shown the system 1100 includes an eye lens 1102 and eyeglasses 1103. The eye lens 1102 includes a piezo element 1108 in communication with a microcontroller 1106. The microcontroller 1106 is in communication with an NFC tag 1104. The NFC tag 1104 can be connected to or can include, for example, a coil shaped antenna 1110 that can communicate with another antenna 1110, such as a coil shaped antenna, on the eyeglasses 1103. NFC communication can include, for example, tunnel mode communication or RF communication. In some embodiments of the invention, the NFC components can send and/or receive power. The NFC tag 1104 can be any NFC tag suitable for receipt of energy through an electromagnetic field and small enough to include on an eye lens in accordance with one or more embodiments of the present invention. In an exemplary embodiment of the invention, the NFC tag 1104 includes memory 1116, an NFC tag microcontroller 1118, and a radio frequency interface (RF-IF) 1112. The eye glasses 1103 contain an NFC Reader/writer 1120 in communication with an NFC Reader/writer microcontroller 1126, memory 1124, and a power supply 1128, such as a battery. In some embodiments of the invention, a microphone 1122 can be included on the eye glasses 1103. However, in some embodiments of the invention, not shown, the system can include a microphone and/or a microcontroller on the eye lens or on other devices. For example, a microphone and/or microcontroller can be embedded or positioned upon an ear, a smart phone, a nose clip, a PC, a tablet or similar external devices. In some embodiments of the invention, data can be transmitted between the eye glasses and eye lens through NFC.

Figure 12:
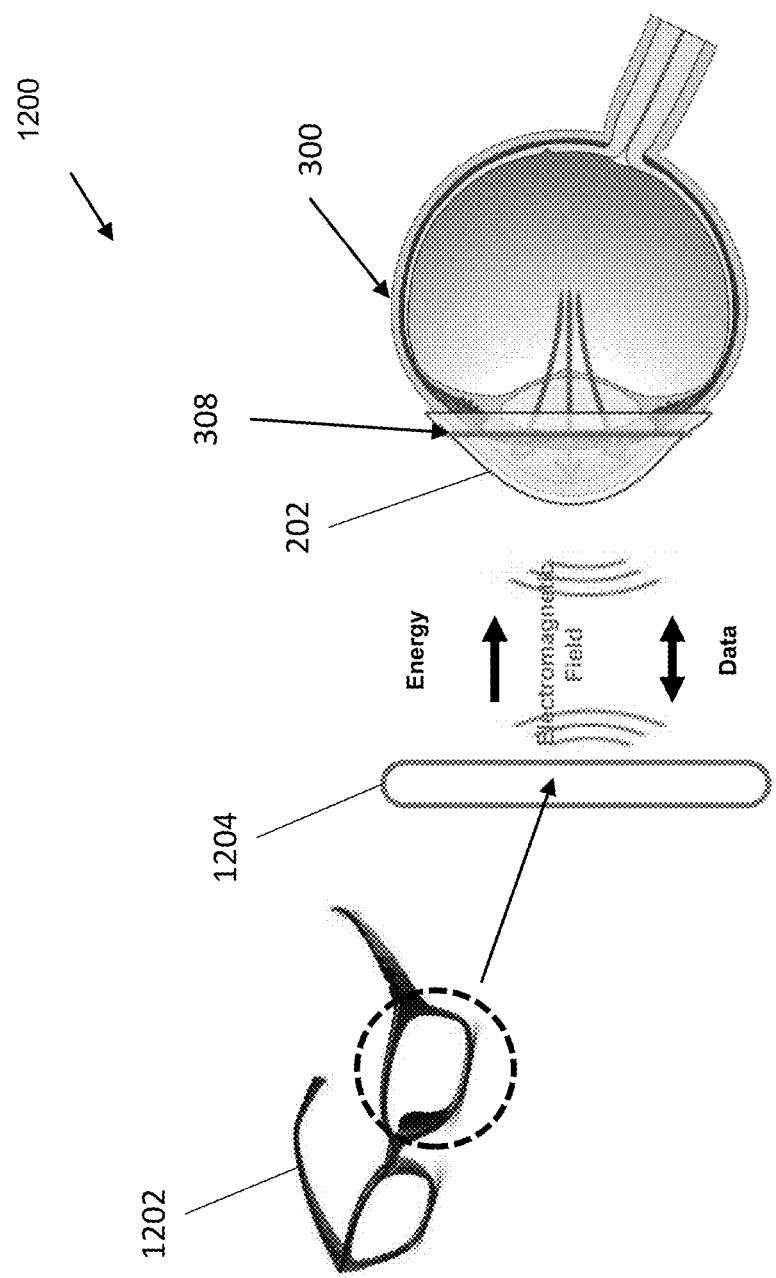
FIG. 12 depicts an eye-based hearing system according to one or more embodiments of the present invention.

FIG. 12 illustrates an exemplary eye-based hearing system 1200 according to one or more embodiments of the present invention including eye glasses 1202 with NFC components. As is shown, an eye lens 202 including a plurality of components 308 can be placed upon an eye 300. The eyeglasses 1202 can include a power source and an NFC reader/writer 1204 that can transmit energy via NFC to the eye lens 202. In some embodiments of the invention, data can be transmitted to and/or from the eye lens from the eye glasses 1202.

Figure 13:
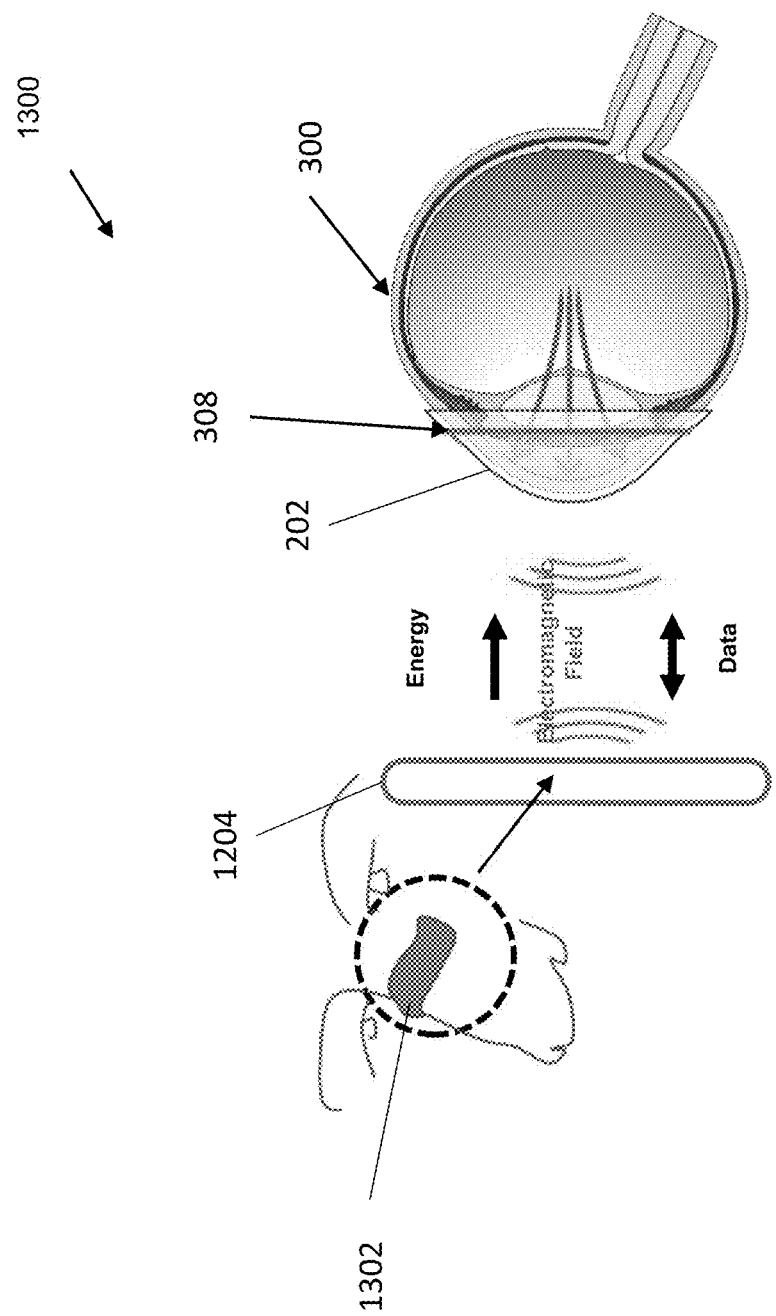
FIG. 13 depicts an eye-based hearing system according to one or more embodiments of the present invention.

FIG. 13 illustrates another exemplary eye-based hearing system 1300 according to one or more embodiments of the present invention including a nose clip 1302 with NFC components. As is shown, an eye lens 202 including a plurality of components 308 can be placed upon an eye 300. The nose clip 1302 can include a power source and an NFC reader/writer 1204 that can transmit energy via NFC to the eye lens 202. In some embodiments of the invention, data can be transmitted to and/or from the eye lens from the nose clip 1202.

Figure 14:
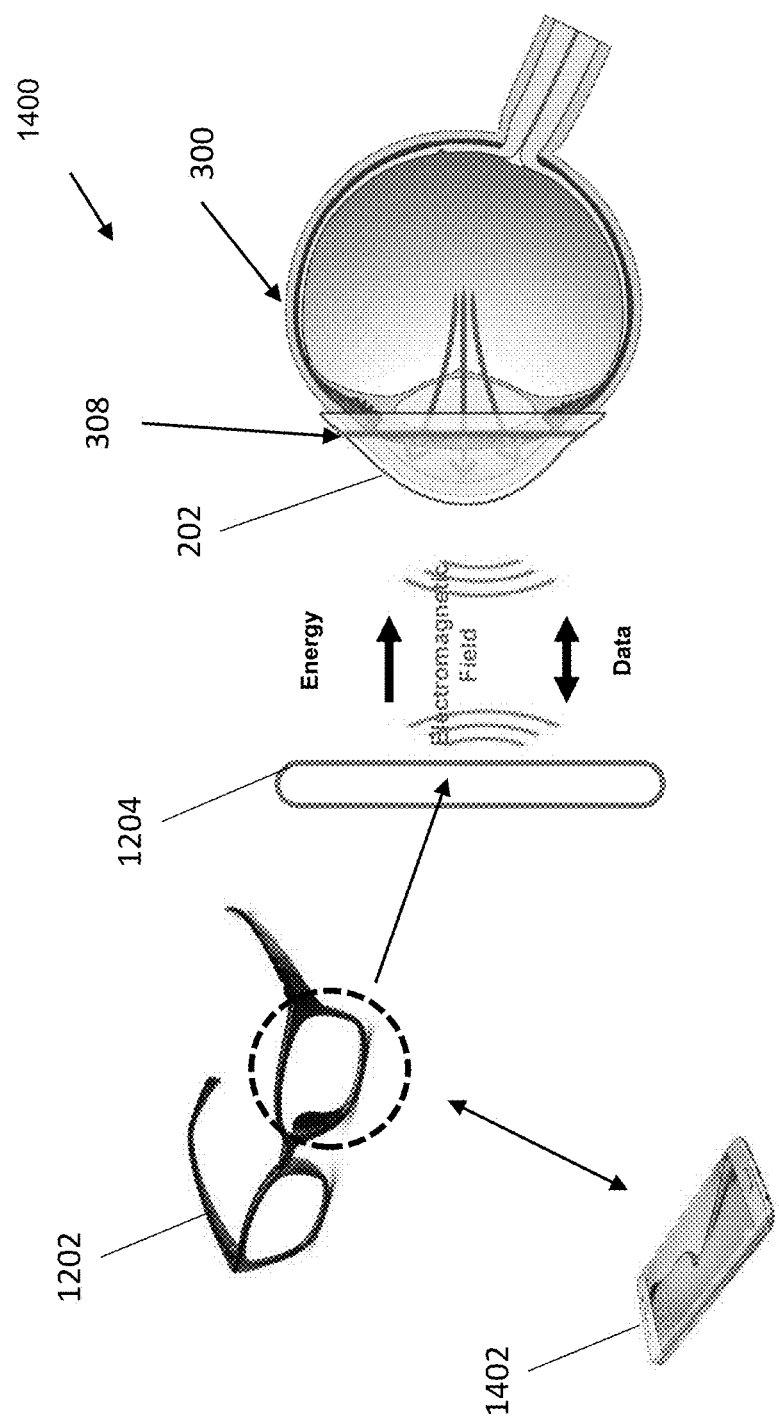
FIG. 14 depicts an eye-based hearing system according to one or more embodiments of the present invention.

FIG. 14 illustrates an exemplary eye-based hearing system 1400 according to one or more embodiments of the present invention including an external device 1402. As is shown, an eye lens 202 including a plurality of components 308 can be placed upon an eye 300. The eye glasses 1202 can include a power source and an NFC reader/writer 1204 that can transmit energy via NFC to the eye lens 202. In some embodiments of the invention, data can be transmitted to and/or from the eye lens from the eye glasses 1202. The system 1400 also includes an external device 1402, such as a smartphone, a wearable device, or portable device, such as a watch, that can communicate with the eye glasses 1202. For example, the external device 1402 can include a microphone and/or microprocessor to transduce sound to digital signals for stimulation of piezo elements on the eye lens.

Figure 15:
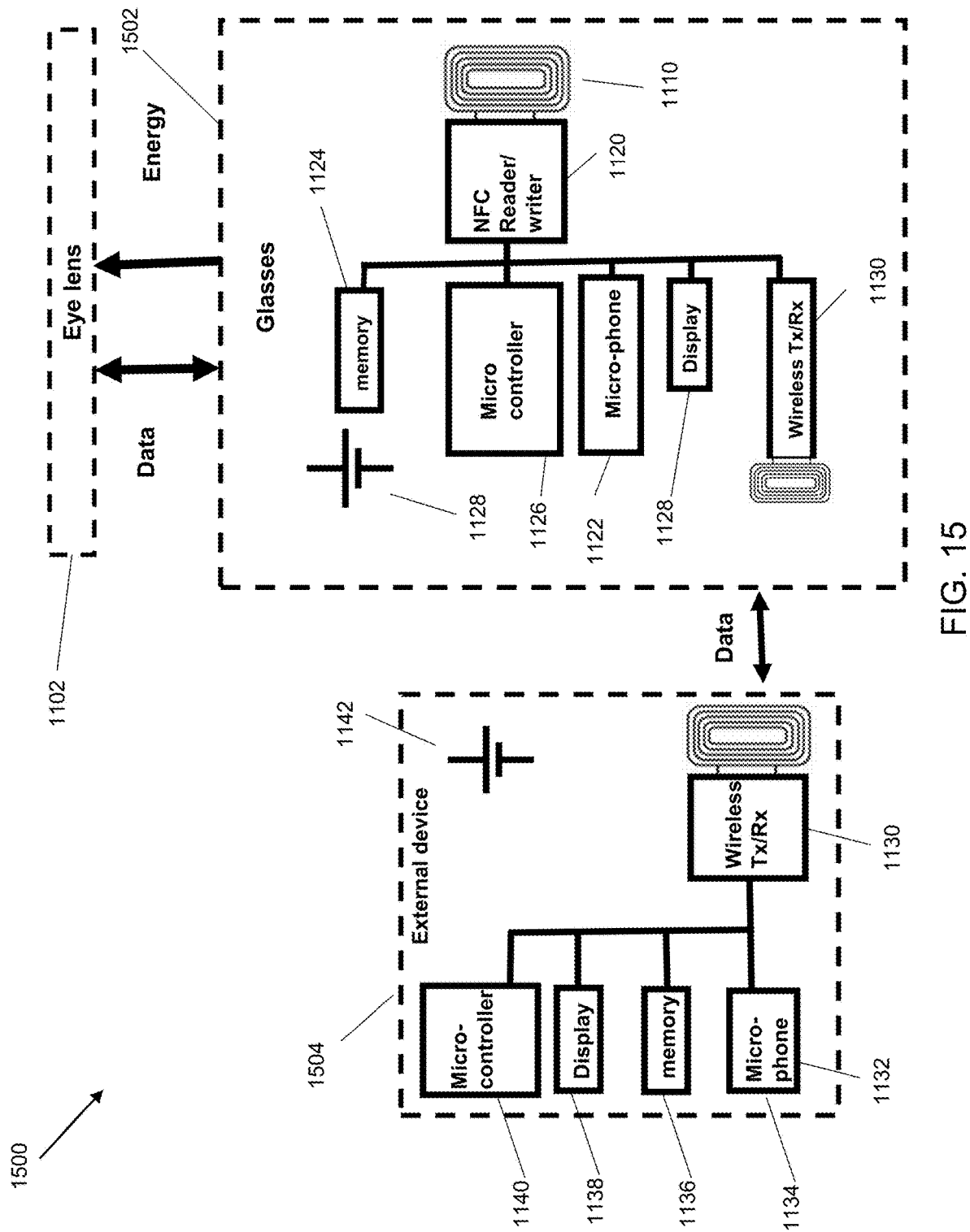
FIG. 15 depicts an eye-based hearing system according to one or more embodiments of the present invention.

FIG. 15 depicts a schematic of an eye-based hearing system 1500 according to one or more embodiments of the invention including multiple devices external to an eye lens, including for instance glasses 1502 in contact with an eye lens 1102 and a second external device 1504 in communication with the glasses 1502. In some embodiments, not shown, an external device in communication with an eye lens 1102 and a second external device can include a nose clip. For example, an exemplary system can include an eye lens combined with eye glasses and a smart phone, eyeglasses and a tablet, other combinations of devices. The external devices are chosen such that an NFC reader/writer 1120 and related antenna is placed in proximity to the eye lens 1102 such that energy can be transferred to the eye lens from the plurality of external devices. In some embodiments of the invention, as shown in FIG. 15, the system 1500 includes an eye lens 1102, glasses 1502, and an external device 1504, such as a tablet or a smart phone. The glasses 1502 can include a coiled antenna 1110 in communication with an NFC Reader/writer 1120 in communication with a microcontroller 1126, memory 1124, a power supply 1128, an optional display 1128, and an optional microphone 1122. For example, the display 1128 can be included within the lenses of the glasses 1502 to display text or visual signals on the lens, for instance to provide textual or visual information pertaining to sounds or system status, such as words or lights displaying battery life. The glasses 1502 can also include wireless transmission components 1130, such as Bluetooth components, for transferring data to or from an external device 1504. In some embodiments of the invention, the external device 1504 includes a microcontroller 1140, display 1138, such as the display of a smart device, PC, or tablet, memory 1136, a micro-phone 1132, and wireless transmission components 1130 capable of communicating with the glasses 1502, such as Bluetooth components.

In some embodiments of the invention, the system can transmit information to the brain of a wearer of an eye lens though stimulation of the cornea by a piezo element in the form of a signal, such as a signal of dots and dashes according to Morse code.

In some embodiments of the invention, the system can transmit information to the wearer of an eye lens through stimulation of the cornea by a piezo element to provide a directional alert, such as a notification of vehicles approaching from a particular direction, or an emergency alert, such as a notification of a siren.

Thus, embodiments of the invention can leverage the high sensitivity of the cornea to provide sound information to the brain of hearing impaired individuals without the need for costly and invasive surgery. Moreover, embodiments of the invention can provide a device for hearing assistance that is convenient for a wearer to use and is light weight. Some embodiments of the invention provide hearing aids that can be discrete and that include components generally worn or used by individuals with no hearing impairments.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A system for stimulating the cornea, the system comprising:
   an eye lens comprising a plurality of piezo elements, each of the plurality of piezo elements comprising a piezoelectric structure that vibrates at a different resonant frequency; and
   an external device wirelessly coupled to the eye lens, the external device comprising a microphone and a microcontroller, the microphone configured to receive an auditory signal;
   wherein the microcontroller is configured to:
      identify a frequency in the auditory signal;
      determine a resonant frequency associated with the frequency; and
      selectively activate one of the plurality of piezo elements based on the resonant frequency; and
   wherein each of the plurality of piezo elements are configured to mechanically simulate a unique region of the cornea upon activation.

2. The system of claim 1, wherein the external device further comprises a power supply in electrical communication with the plurality of piezo elements.

3. The system of claim 2, wherein the external device further comprises a near field communication (NFC) component.

4. The system of claim 3, wherein the NFC component is configured with an antenna to wirelessly transfer energy to the eye lens.

5. The system of claim 4, wherein the eye lens further comprises a second NFC component communicatively coupled to the NFC component on the external device.

6. The system according to claim 5, wherein the NFC component comprises an NFC reader and the second NFC component comprises an NFC tag.

7. The system of claim 1, wherein the external device comprises eye glasses.

8. The system of claim 1, wherein the external device comprises a nose clip.

9. The system of claim 1, wherein the external device comprises a smartphone.

10. The system according to claim 1, further comprising a memory in communication with the microcontroller.

11. A method for stimulating the cornea, the method comprising:
- providing an eye lens comprising a plurality of piezo elements, each of the plurality of piezo elements comprising a piezoelectric structure that vibrates at a different resonant frequency;
- providing an external device wirelessly coupled to the eye lens, the external device comprising a microphone and a microcontroller, the microphone configured to receive an auditory signal;
- identifying, by the microcontroller, a frequency in the auditory signal;
- determining, by the microcontroller, a resonant frequency associated with the frequency; and
- selectively activating, by the microcontroller, one of the plurality of piezo elements based on the resonant frequency;
- wherein each of the plurality of piezo elements are configured to mechanically simulate a unique region of the cornea upon activation.

12. The method of claim 11, wherein the external device further comprises a power supply in electrical communication with the plurality of piezo elements.

13. The method of claim 12, wherein the external device further comprises a near field communication (NFC) component.

14. The method of claim 13, wherein the NFC component is configured with an antenna to wirelessly transfer energy to the eye lens.

15. The method of claim 14, wherein the eye lens further comprises a second NFC component communicatively coupled to the NFC component on the external device.

16. The method according to claim 15, wherein the NFC component comprises an NFC reader and the second NFC component comprises an NFC tag.

17. The method of claim 11, wherein the external device comprises eye glasses.

18. The method of claim 11, wherein the external device comprises a nose clip.

19. The method of claim 11, wherein the external device comprises a smartphone.

20. The method according to claim 11, further comprising a memory in communication with the microcontroller.

* * * * *